(12) United States Patent
Eby et al.

(10) Patent No.: US 11,027,119 B2
(45) Date of Patent: Jun. 8, 2021

(54) SYSTEMS AND METHODS FOR IMPLANTING A MEDICAL DEVICE

(71) Applicant: Pacesetter, Inc., Santa Clara, CA (US)

(72) Inventors: Thomas B. Eby, Mountain View, CA (US); Alan Klenk, San Jose, CA (US)

(73) Assignee: PACESETTER, INC., Sylmar, CA (US)

( * ) Notice: Subject to any disclaimer, the term of this patent is extended or adjusted under 35 U.S.C. 154(b) by 63 days.

(21) Appl. No.: 16/189,891

(22) Filed: Nov. 13, 2018

(65) Prior Publication Data

US 2019/0111248 A1    Apr. 18, 2019

Related U.S. Application Data

(62) Division of application No. 14/481,818, filed on Sep. 9, 2014, now Pat. No. 10,716,931.

(51) Int. Cl.

| | |
|---|---|
| *A61N 1/00* | (2006.01) |
| *A61N 1/05* | (2006.01) |
| *A61N 1/375* | (2006.01) |
| *A61N 1/372* | (2006.01) |
| A61B 17/00 | (2006.01) |
| A61B 17/34 | (2006.01) |
| A61M 25/00 | (2006.01) |

(52) U.S. Cl.
CPC ............. *A61N 1/05* (2013.01); *A61N 1/3756* (2013.01); *A61N 1/37205* (2013.01); A61B 17/3468 (2013.01); A61B 2017/00473 (2013.01); A61M 25/0082 (2013.01); A61N 2001/058 (2013.01)

(58) Field of Classification Search
CPC ...... A61N 2001/0578; A61N 2001/058; A61N 1/37205; A61N 1/05; A61N 1/3756; A61B 17/3468; A61B 2017/00473; A61M 25/0082
See application file for complete search history.

(56) References Cited

U.S. PATENT DOCUMENTS

| | | | |
|---|---|---|---|
| 6,059,719 | A | 5/2000 | Yamamoto |
| 6,149,664 | A | 11/2000 | Kurz |

(Continued)

OTHER PUBLICATIONS

Non-Final Office Action dated Jun. 2, 2017; Related U.S. Appl. No. 14/481,799.

(Continued)

*Primary Examiner* — Steven O Douglas
(74) *Attorney, Agent, or Firm* — Womble Bond Dickinson (US) LLP

(57) ABSTRACT

In at least one embodiment, a system and method for implanting an implantable medical device (IMD) within a patient may include an IMD including a housing and an attachment member, and a delivery catheter including a tethering snare that is configured to be selectively extended out of the delivery catheter and retracted into the delivery catheter. In at least one embodiment, a system and method for implanting an implantable medical device (IMD) within a patient may include an IMD including a housing and an attachment member, wherein the attachment member includes a central passage connected to a connection chamber, and a delivery catheter including first and second tethers that may be moved outwardly from and retracted into the delivery catheter.

13 Claims, 16 Drawing Sheets

(56) References Cited

U.S. PATENT DOCUMENTS

| | | |
|---|---|---|
| 8,377,044 B2 | 2/2013 | Coe |
| 2006/0243106 A1 | 11/2006 | Kikuchi |
| 2008/0243106 A1 | 10/2008 | Coe |
| 2009/0204170 A1* | 8/2009 | Hastings .............. A61N 1/3684 607/33 |
| 2012/0165827 A1* | 6/2012 | Khairkhahan ......... A61N 1/059 606/129 |
| 2012/0197373 A1* | 8/2012 | Khairkhahan ....... A61N 1/0573 607/127 |
| 2014/0074114 A1 | 3/2014 | Khairkhahan |
| 2015/0051611 A1* | 2/2015 | Schmidt .............. A61B 17/064 606/129 |

OTHER PUBLICATIONS

Final Office Action dated Jul. 13, 2018; Related U.S. Appl. No. 14/481,818.
Amendment filed Mar. 1, 2018; Related U.S. Appl. No. 14/481,818.
Non-Final Office Action dated Dec. 27, 2017; Related U.S. Appl. No. 14/481,818.

* cited by examiner

SYSTEMS AND METHODS FOR IMPLANTING A MEDICAL DEVICE

PRIORITY CLAIM

This application is a Divisional application of U.S. patent application Ser. No. 14/481,818, filed Sep. 9, 2014, of which is incorporated herein by reference in its entirety to provide continuity of disclosure.

BACKGROUND

Embodiments of the present disclosure generally relate to implantable medical devices, and, more particularly, to systems and methods for implanting a medical device.

Numerous medical devices exist today, including but not limited to electrocardiographs ("ECGs"), electroencephalographs ("EEGs"), squid magnetometers, implantable pacemakers, implantable cardioverter-defibrillators ("ICDs"), neurostimulators, electrophysiology ("EP") mapping and radio frequency ("RF") ablation systems, and the like. Implantable medical devices (hereafter generally "implantable medical devices" or "IMDs") are configured to be implanted within patient anatomy and commonly employ one or more leads with electrodes that either receive or deliver voltage, current or other electromagnetic pulses (generally "energy") from or to an organ or tissue for diagnostic or therapeutic purposes.

Typically, an intra-cardiac IMD is introduced into the heart through a catheter. However, trans-catheter delivery of an entire IMD within a heart typically requires specialized tools. Often, the specialized tools are complex and may be difficult to manipulate and operate.

In general, an IMD may be connected to a delivery system in a docked state, in which the IMD is securely attached to the delivery system. In the docked state, the catheter may be operated to guide the IMD to an implant site. Once the IMD is proximate to the implant site, because the IMD is securely connected to the catheter, the catheter may be used to torque the IMD into patient tissue.

Once the IMD is secured into patient tissue, the IMD may be moved into a tethered state with respect to the catheter. In the tethered state, the catheter separates from the IMD, but remains connected thereto. In the tethered state, an implanting physician may test the IMD to make sure that the IMD is securely and electrically connected to patient tissue at a desired location. If the physical and/or electrical connection between the IMD and the patient tissue is less than optimal, the IMD may be re-docked to the catheter so that that the IMD may be moved to a better position for implantation.

Once the implanting physician is satisfied with the location of the IMD within patient anatomy, the IMD is transitioned from the tethered state to a release state. In the release state, the IMD disconnects from the catheter.

However, known systems and methods for releasing an IMD from a catheter are often susceptible to spontaneous release, in which the IMD inadvertently releases from the catheter. Further, known release systems and methods may not release the IMD smoothly and easily from the catheter. Also, known release systems and methods may malfunction and fail to release the IMD from the catheter.

SUMMARY

Certain embodiments provide a system for implanting an IMD within a patient. The system may include an IMD including a housing and an attachment member. The system may also include a delivery catheter including a tethering snare that is configured to be selectively extended out of the delivery catheter and retracted into the delivery catheter. The tethering snare may be configured to fit over at least a portion of the attachment member in a fully extended position. Further, the tethering snare may be configured to securely tether to the attachment member in a retracted position. The tethering snare may be operable to retrievably connect the IMD to the delivery catheter, and release the IMD from the delivery catheter.

In at least one embodiment, the tethering snare forms a loop that extends out of the delivery catheter. The loop is configured to fit over the portion of the attachment member in the fully extended position. The loop is configured to constrict around the portion of the attachment member in the retracted position. A size of the loop may increase when the tethering snare is extended out of the delivery catheter. The size of the loop may decrease when the tethering snare is retracted into the delivery catheter.

The attachment member may include a neck extending from the housing, and an expanded head connected to the neck. The tethering snare may be configured to fit over the expanded head in the fully extended position, and securely constrict around the neck proximate to the expanded head in the retracted position. In at least one embodiment, the neck is pivotally secured to the housing. The attachment member may also include at least one torque recess, and the delivery catheter may include at least one torque key. The torque recess(es) is configured to securely mate with the torque key(s) in a docked state.

Certain embodiments of the present disclosure provide a method for implanting an IMD within a patient. The method may include extending a tethering snare out of a delivery catheter to fit over a portion of an attachment member of the IMD, moving the extended tethering snare over the portion of the attachment member to a connecting position, retracting the tethering snare into the delivery catheter to securely connect the tethering snare to the IMD at the connecting position, and releasing the IMD from the delivery catheter by extending the tethering snare out of the delivery catheter so that the tethering snare disengages from the connecting position, and removing the tethering snare from the attachment member.

Certain embodiments of the present disclosure provide a system for implanting an implantable medical device (IMD) within a patient. The system may include an IMD including a housing and an attachment member. The attachment member may include a central passage connected to a connection chamber. The system may also include a delivery catheter including first and second tethers that may be moved outwardly from and retracted into the delivery catheter. The first tether may include a protuberance at a distal end. The protuberance is sized to pass into the central passage. The protuberance and the second tether are configured to be lodged into one or both of the central passage and the connection chamber to securely tether the IMD to the delivery catheter.

The second tether may include an elongated interfering segment that is configured to be retracted into the delivery catheter and removed from the central passage. The protuberance may be removed from the central passage in response to the elongated interfering segment being removed from the central passage. In at least one embodiment, the second tether may be featureless and devoid of any protuberance.

A protuberance diameter of the protuberance may be less than a passage diameter of the central passage. A tether diameter of the second tether may be less than either of the passage diameter and the protuberance diameter. A combined diameter of the tether diameter and the protuberance diameter may be greater than the passage diameter.

Certain embodiments of the present disclosure provide a method for implanting an IMD within a patient. The method may include securing the IMD to a delivery catheter by positioning a first tether within a central passage of an attachment member of the IMD. The positioning the first tether within the central passage prevents a protuberance of a second tether from passing into the central passage. The method may also include releasing the IMD from the delivery catheter by removing the first tether from the central passage. The removing the first tether from the central passage allows the protuberance to be removed from the central passage.

DETAILED DESCRIPTION

Embodiments of the present disclosure provide systems and methods of attaching an IMD to a catheter, and disconnecting the IMD from the catheter in an intuitive, straightforward, and easy manner. The IMD may be any one of various types of implantable devices, such as, for example, an implantable pacemaker, implantable cardioverter-defibrillator ("ICD"), defibrillator, cardiac rhythm management ("CRM") device, neurostimulator, or the like.

In at least one embodiment, the IMD may include a leadless cardiac pacemaker that may be enclosed in a hermetic housing or can that may be positioned on the inside or outside of a cardiac chamber. The pacemaker may have two or more electrodes located within, on, or near the housing, for delivering pacing pulses to muscle of the cardiac chamber and optionally for sensing electrical activity from the muscle, and for bidirectional communication with at least one other device within or outside the body. The housing may contain a primary battery to provide power for pacing, sensing, and communication, for example bidirectional communication. The housing may optionally contain circuits for sensing cardiac activity from the electrodes. The housing may contain circuits for receiving information from at least one other device via the electrodes and may contain circuits for generating pacing pulses for delivery via the electrodes. The housing may optionally contain circuits for transmitting information to at least one other device via the electrodes and may optionally contain circuits for monitoring device health. The housing may contain circuits for controlling these operations in a predetermined manner.

Figure 1:
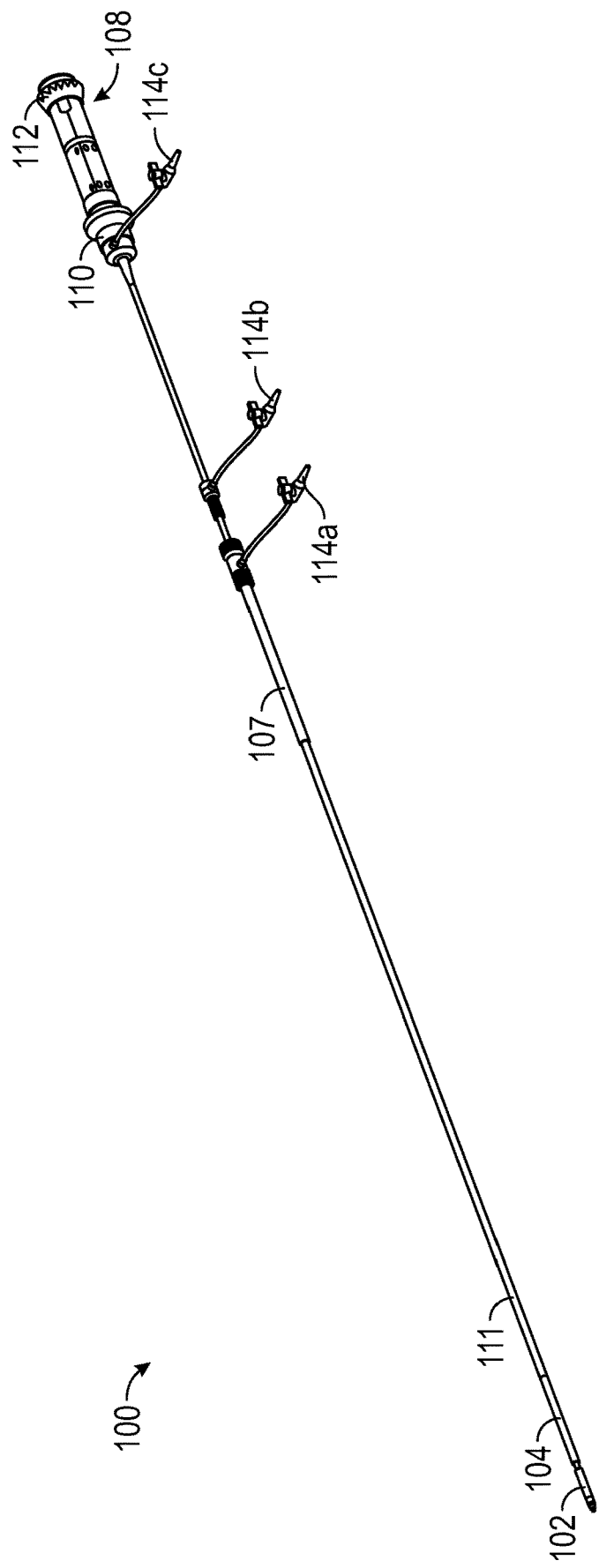
FIG. 1 illustrates a perspective view of a delivery system for delivering an implantable medical device (IMD) into a patient, according to an embodiment of the present disclosure.

FIG. 1 illustrates a perspective view of a delivery system 100 for delivering an IMD 102 into a patient, according to an embodiment of the present disclosure. The delivery system 100 may include an IMD sheath 104, a guide catheter 111, an introducer sheath 107, a handle 108, a deflection knob 110, a tether shuttle 112, and flush ports 114a, 114b, and 114c. The deflection knob 110 may be used to steer and guide the catheter 111 during implantation and/or removal of the IMD 102. The flush ports 114a, 114b, and 114c may be used to flush saline or other fluids through the catheter 111. The introducer sheath 107 may be advanced distally over the catheter 111 to provide additional steering and support for the catheter 111 during implantation and to surround the IMD 102 as it is introduced through a trocar or introducer into a patient.

Figure 2A:
FIG. 2A illustrate a perspective view of a distal portion of a delivery system and an IMD, according to an embodiment of the present disclosure.

FIG. 2A illustrate a perspective view of a distal portion of a delivery system 200 and an IMD 202, according to an embodiment of the present disclosure. The IMD 200 may include a helix 203 that may be used to attach the IMD 200 to tissue of a patient. The IMD 202 may include an attachment member that is configured to removably connect to a docking cap 218 of a catheter 206. An IMD sheath 204 is shown pulled back proximally along the catheter 206 and a guide shaft 211 to expose the IMD 202 and the helix 203.

Figure 2B:
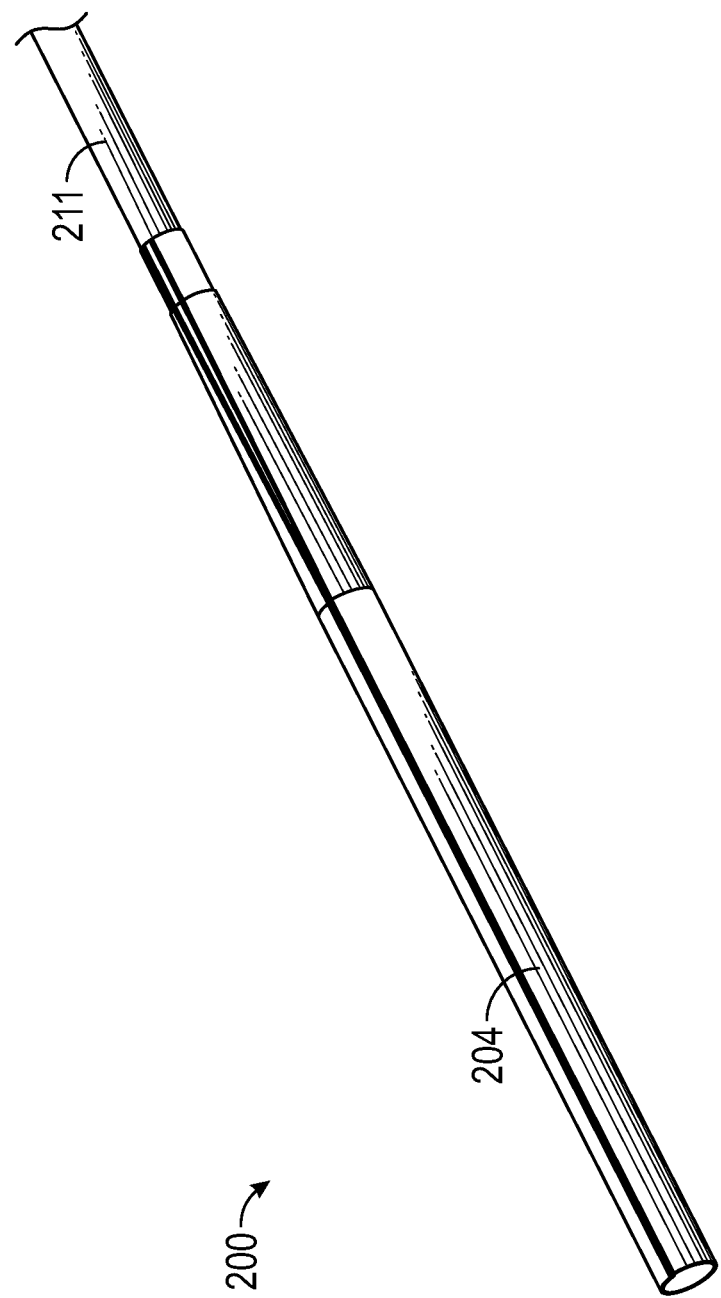
FIG. 2B illustrates a perspective view of an IMD sheath extended distally along a guide shaft, according to an embodiment of the present disclosure.

FIG. 2B illustrates a perspective view of the IMD sheath 204 extended distally along the guide shaft 211 to cover the catheter 206, the IMD 202, and the helix 203, according to an embodiment of the present disclosure. The extended IMD sheath 204 protects patient tissue from sharp edges of the helix 203 during implantation. Referring to FIGS. 2A and 2B, when the IMD sheath 204 is pulled back proximally, as shown in FIG. 2A, the IMD 202 is in an exposed, delivery configuration. When the IMD sheath 204 is advanced distally to protect the IMD 202 and the helix 203, as shown in FIG. 2B, the IMD 202 is in a protected, advancement configuration.

Figure 3A:
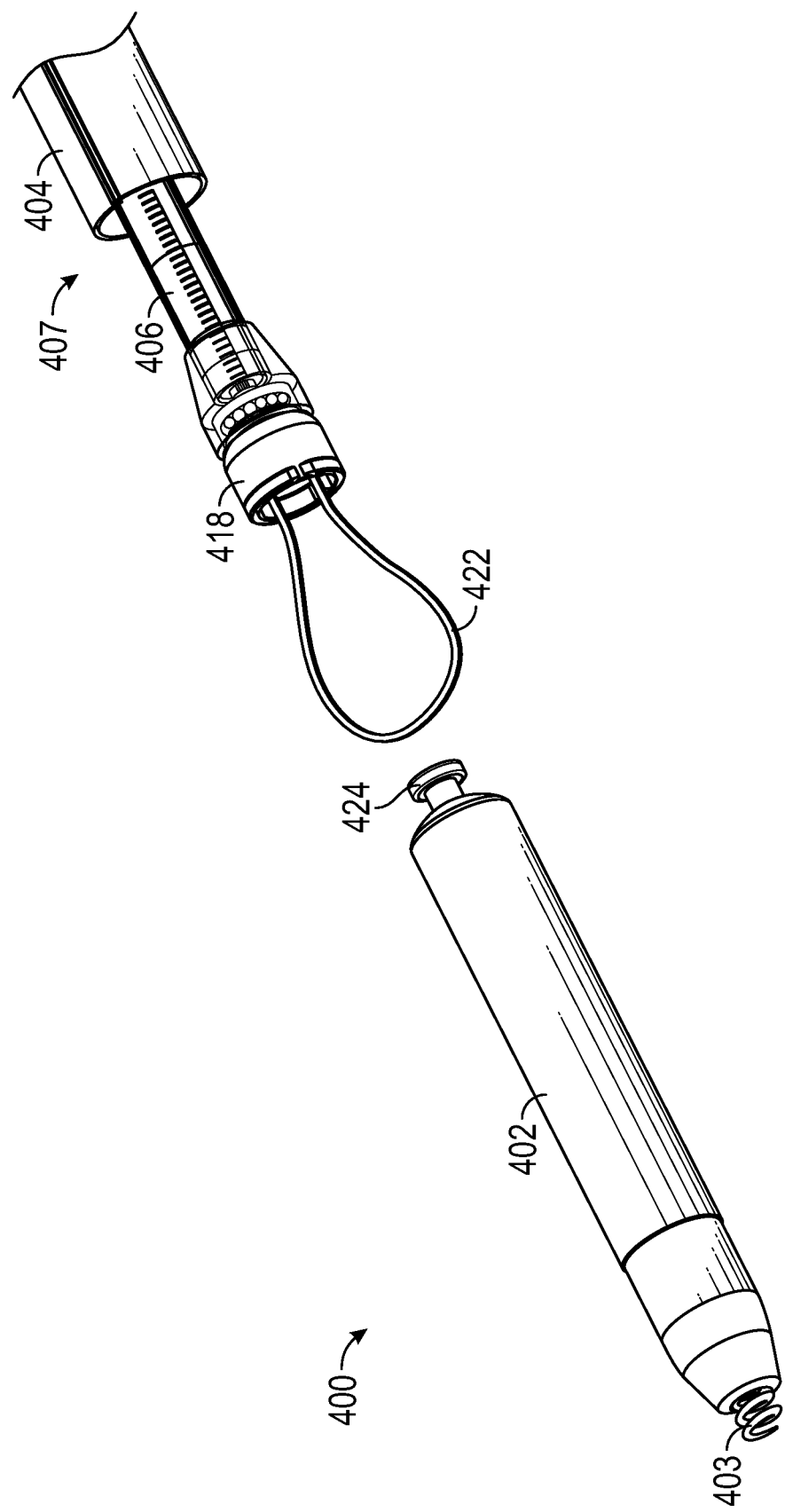
FIG. 3A illustrates a perspective view of a delivery system disconnected from an IMD, according to an embodiment of the present disclosure.

FIG. 3A illustrates a perspective view of a delivery system 400 disconnected from an IMD 402, according to an embodiment of the present disclosure. The delivery system 400 may include the IMD 402 when the IMD 402 is connected to the delivery system 400. The IMD 402 may include a helix 403 and an attachment member 424, such as a docking button, cap, stud, ridge, ledge, rim or the like.

The delivery system 400 may include a delivery catheter 407 that may include an IMD sheath 404, a catheter shaft 406, a docking cap 418, and a tethering snare 422. The tethering snare 422 may be or include one or more wires, shafts, tubes, cords, ropes, strings, or other similar structures that may extend throughout the catheter shaft 406. In at least one embodiment, the tethering snare 422 may include a shape memory material, such as nitinol. In other embodiments, the tethering snare 422 may include stainless steel wires or braids. As shown in FIG. 3A, the IMD 402 is disconnected from the docking cap 418 of the delivery catheter 407.

Figure 3B:
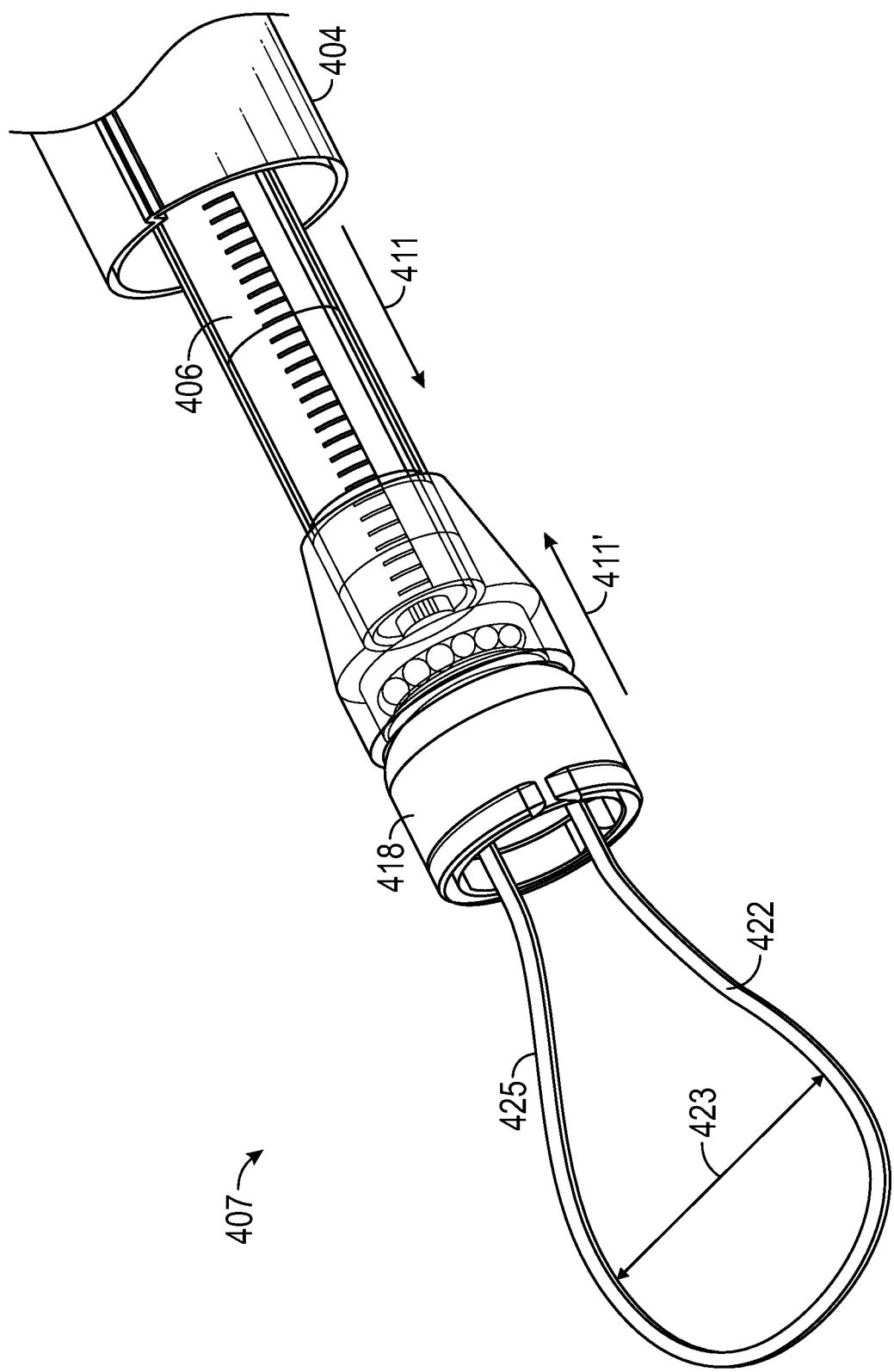
FIG. 3B illustrates a perspective view of a distal end of a delivery catheter, according to an embodiment of the present disclosure.

FIG. 3B illustrates a perspective view of a distal end of the delivery catheter 407, according to an embodiment of the present disclosure. The tethering snare 422 is configured to be moved into and out of the delivery catheter 407 to expand its size. For example, the tethering snare 422 may be extended out of the docking cap 418 to expand a diameter 423 of a loop 425 of the tethering snare 422, as described in detail below. In at least one embodiment, the IMD sheath 404 of the delivery catheter 407 may be moved over the tethering snare 407 over the catheter shaft 406 in the direction of arrow 411 in order to reduce the size of the tethering snare 422. As the IMD sheath 404 retreats back over the catheter shaft 406 in the direction of 411', the size of the tethering snare 422 increases. The expanded tethering snare 422 is used to loop over and snare the attachment member 424 (shown in FIG. 3A). Once the attachment member 424 is snared, the tethering snare 422 is pulled back into the delivery catheter 407 (such as by an operator pulling the proximal ends of the tethering snare 422 into the delivery catheter 407, and/or the IMD sheath 404 being moved over the tethering snare 422 in the direction of arrow 411) in order to securely tether the IMD to the delivery catheter 407, as described in detail below.

In at least one embodiment, the delivery catheter 407 may include a locking sheath (which may be or form part of the IMD sheath 404) that collapses the tethering snare 422. For example, the tethering snare 422 may be formed of a resilient material, such as nitinol. As such, the tethering snare 422 springs back to an at-rest shape when the locking sheath is removed from the tethering snare 422.

Figure 3C:
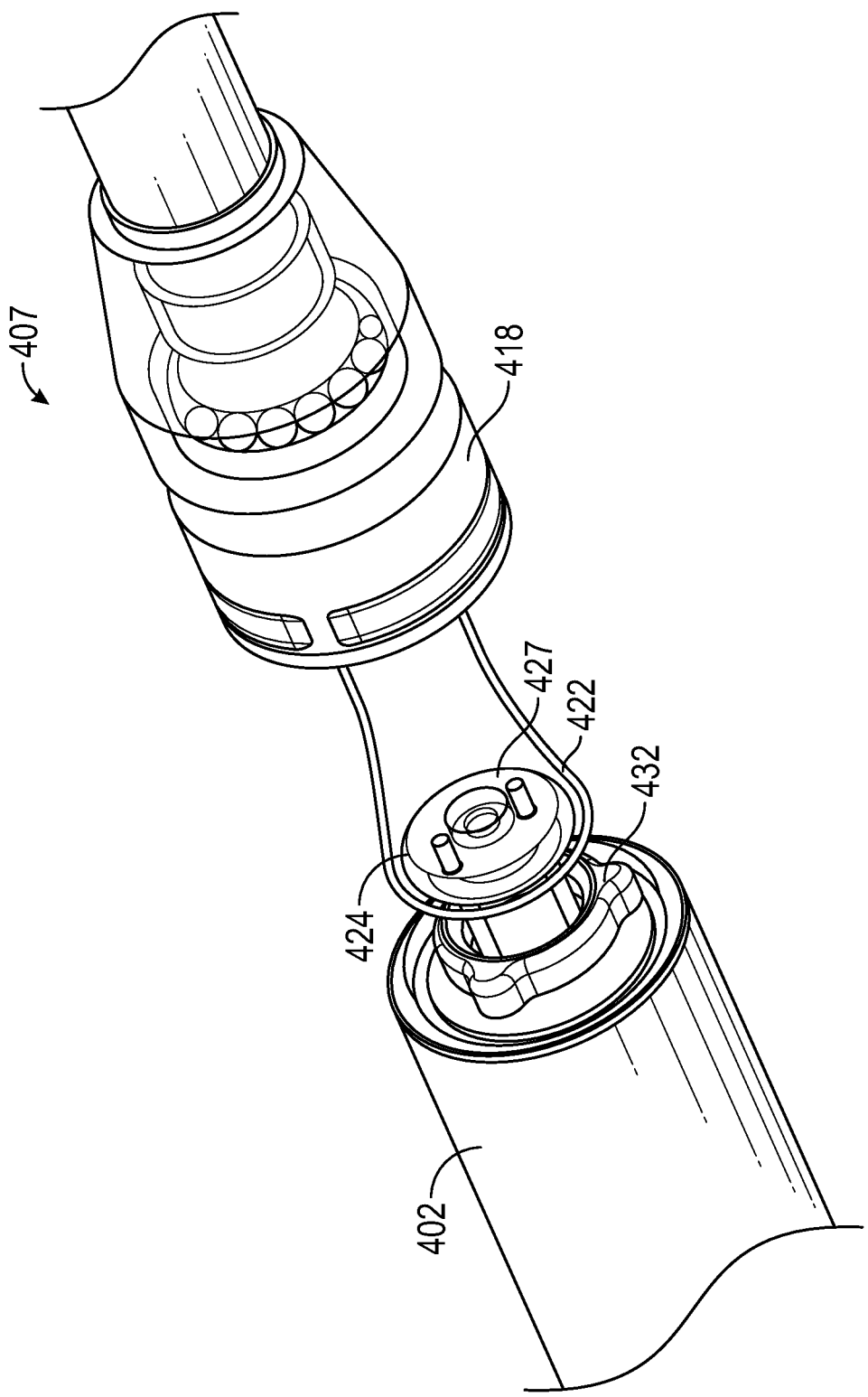
FIG. 3C illustrates a perspective view of a delivery catheter tethered to an IMD, according to an embodiment of the present disclosure.
Figure 3D:
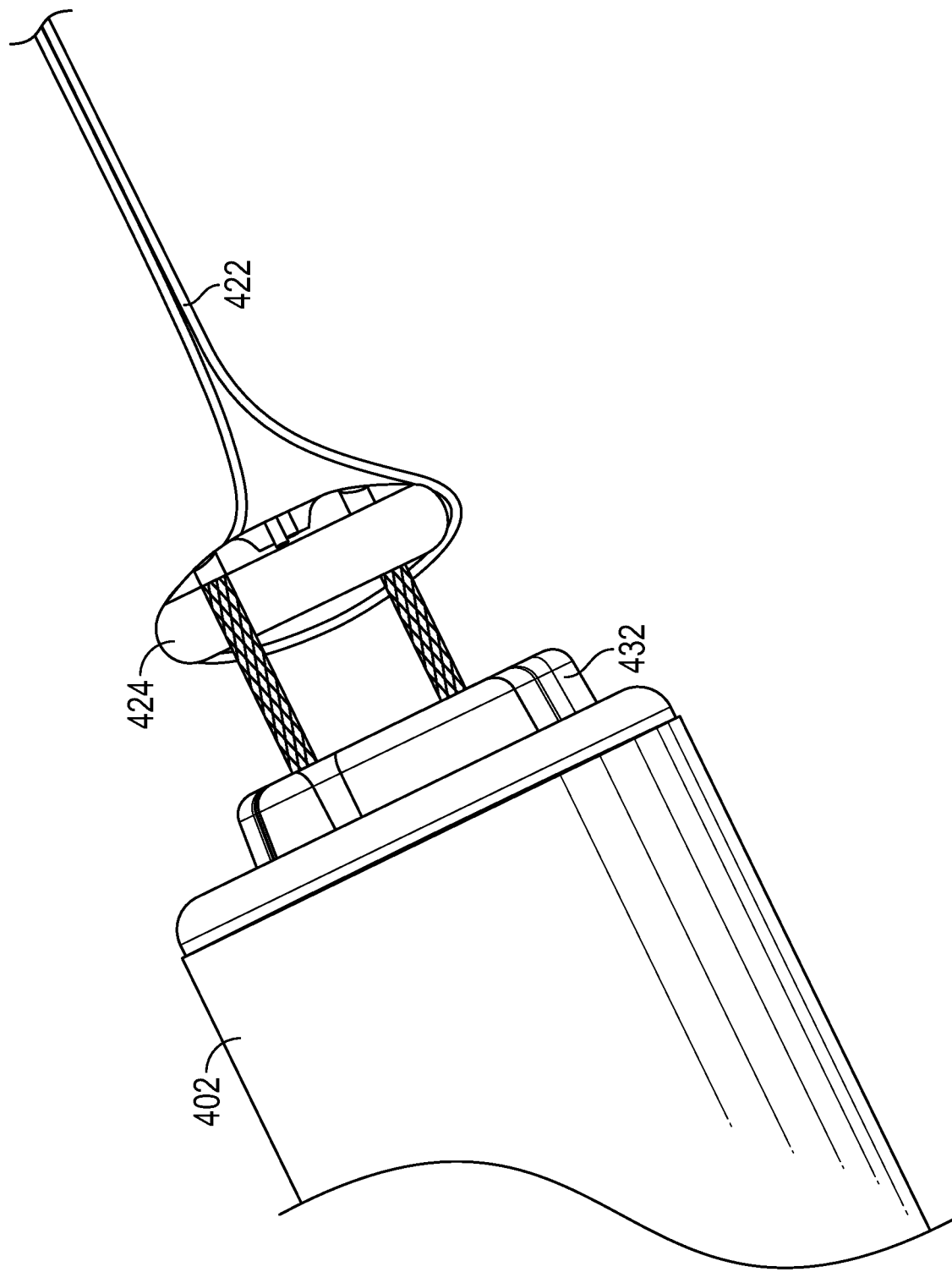
FIG. 3D illustrates a lateral view of a delivery catheter tethered to an IMD, according to an embodiment of the present disclosure.

FIG. 3C illustrates a perspective view of the delivery catheter 407 tethered to the IMD 402, according to an embodiment of the present disclosure. FIG. 3D illustrates a lateral view of the delivery catheter 407 tethered to the IMD 402. Referring to FIGS. 3C and 3D, the tethering snare 422 is positioned underneath a securing member 427, such as a head, stud, block, barb, or the like, of the attachment member 424 so that the loop 425 catches, snags, or snares thereon. After the loop 425 snares onto the attachment member 424, the tethering snare 424 is drawn into the delivery catheter 407 so that the tethering snare 424 securely tethers the IMD 402 to the delivery catheter 407.

The docking cap 418 of the delivery catheter may include a torque slot that is sized and configured to mate with a torque key 432 located on a proximal end of the pacemaker IMD 402. The torque slot may be coupled to a torque shaft, which may run the length of the delivery catheter extending into the handle (not shown). The torque key may be a "male" key and the torque slot may be a "female" key, or vice versa. The torque key and the torque slot may include any number of shapes, such as square, rectangle, triangle, pentagon, hexagon, cross, "X", and the like, so long as the key fits within and can apply rotational torque to the slot. Once the tethering snare 422 securely tethers to the attachment member 424, the tethering snare 422 may be pulled proximally to pull the attachment feature 424 and therefore the IMD 402 towards the delivery catheter 407 and to attach the IMD 402 to the delivery catheter 407, thereby engaging the torque slot with the torque key 432.

Aspects of the delivery catheter 407 and the IMD 402 may be further described in United States Patent Application Publication No. 2014/0074114, entitled "Delivery Catheter Systems and Methods," which is hereby incorporated by reference in its entirety.

Figure 4:
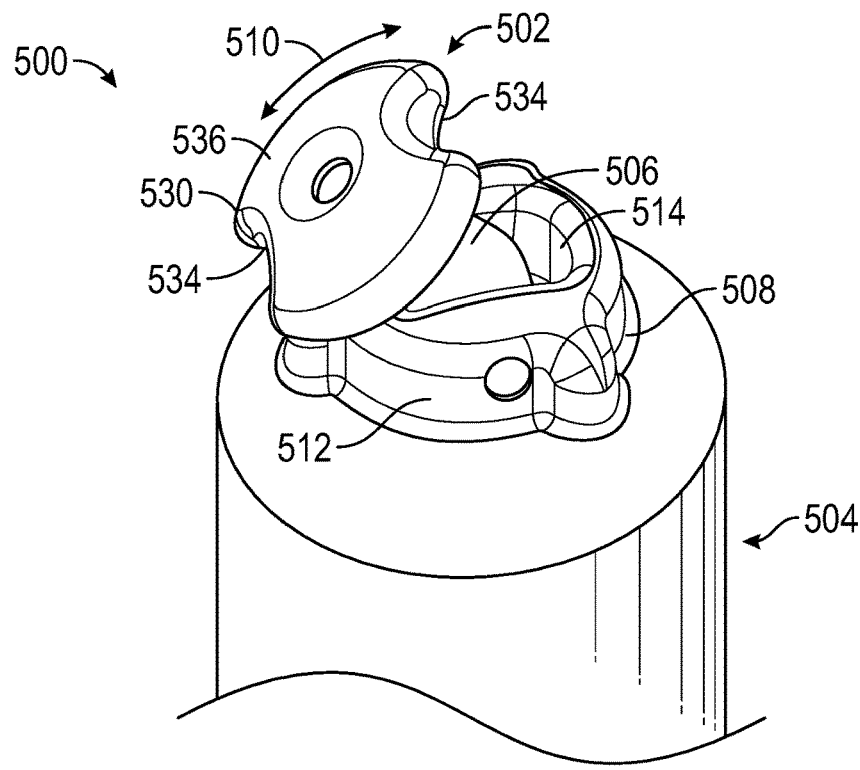
FIG. 4 illustrates a perspective top view of a proximal end of an IMD, according to an embodiment of the present disclosure.

FIG. 4 illustrates a perspective top view of a proximal end of an IMD 500, according to an embodiment of the present disclosure. The IMD 500 may include an attachment member 502 connected to a housing or can 504. The attachment member 502 may be or include a docking button, for example, that is configured to removably connect to a delivery catheter.

The attachment member 502 may include a neck 506 that is pivotally secured to a proximal end of the housing 504 through a central guide pin that is rotatably secured within reciprocal channels formed through a collar 508 that extends upwardly from the housing 504. The rotatable connection between the pin and the channels allows the attachment member 502 to pivot in the directions of arc 510 about an axis defined by the central guide pin. Alternatively, the housing 504 may include the central guide pin, while the neck 506 includes a channel that receives the central guide pin.

The collar 508 includes an outer wall 512 that defined a cavity 514 in which the neck 506 is positioned. The outer wall 512 limits the pivotal movement of the neck within the cavity 514. Alternatively, the housing 504 may not include the collar 508.

Figure 5:
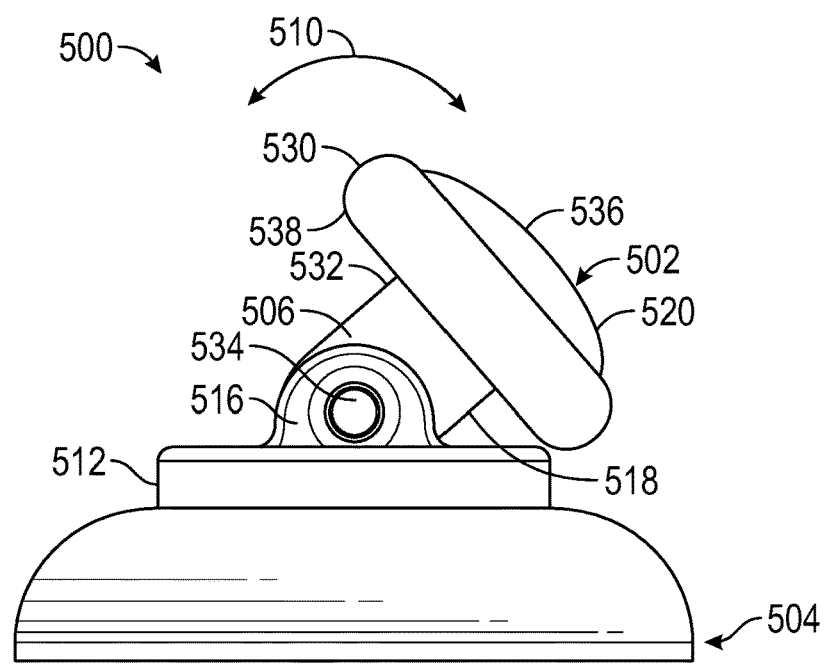
FIG. 5 illustrates a lateral view of a proximal end of an IMD, according to an embodiment of the present disclosure.

FIG. 5 illustrates a lateral view of the proximal end of the IMD 500, according to an embodiment of the present disclosure. As shown in FIG. 5, the neck 506 may include the central guide pin 516 having ends that are pivotally retained within channels formed through brackets 518 extending from the collar 508. Accordingly, the attachment member 502 may pivot in the directions denoted by arc 510 about the central longitudinal axis 520 of the central guide pin 516. The attachment member 502 may pivot in order to allow the IMD 500 to bend, pivot, or otherwise articulate as the IMD 500 is navigated to an implant site. Accordingly, the IMD 500 may be moved with greater ease and precision through vasculature of a patient. Alternatively, the attachment member 502 may be fixed in position, and may not be configured to pivot with respect to the housing 504.

Referring to FIGS. 4 and 5, the attachment member 502 may also include an expanded head 530 connected to an end of the neck 506 that is opposite from an end 534 that pivotally secures to the housing 504. The expanded head 530 may have a diameter that is greater than that of the neck 506. The head 530 may include one or more torque recesses 534, such as divots, cut-outs, cored-out areas, slots, slits, or the like, formed therethrough. The torque recesses 534 may be scalloped areas that allow for increased torque transfer. The torque recesses 534 are configured to mate with reciprocal torque keys within a delivery catheter, as described above. Alternatively, the head 530 may include one or more torque keys, while the delivery catheter includes the torque recesses 534.

Each torque recess 534 may be formed through the head 530 from a top surface 536 to a bottom surface 538. Alternatively, each torque recess 534 may be formed from the top surface 536 to an intermediate area above the bottom surface 538. More or less torque recesses 534 may be used. For example, the head 530 may include a single torque recess, or three or more regularly spaced torque recesses.

Figure 6:
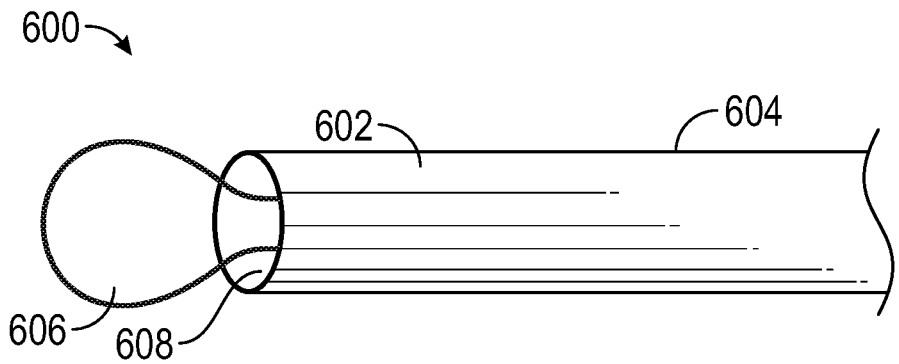
FIG. 6 illustrates a lateral view of a tethering snare extending from a distal end of a delivery catheter, according to an embodiment of the present disclosure.

FIG. 6 illustrates a lateral view of a tethering snare 600 extending from a distal end 602 of a delivery catheter 604, according to an embodiment of the present disclosure. The tethering snare 600 is an example of such as shown and described with respect to FIGS. 3A-3D. The tethering snare 600 may be or include a loop 606 (which may include a single loop or a plurality of loops) of wire, string, or the like that extends outwardly from an internal passage 608 of the delivery catheter 604. Ends of the loop 606 may be operatively connected to a control device, such as the shuttle 112 shown in FIG. 1, a control knob, joystick, button(s), and/or the like of an IMD delivery system, similar to the system 100 shown in FIG. 1. The loop 606 may be drawn into internal passage 608 to decrease its size, or pushed outwardly from the internal passage 608 to increase its size, such as through movement of the tethering snare 600 into and out of the delivery catheter 604, and/or through movement of the delivery catheter 604 or sheath in relation to the tethering snare 600.

The tethering snare 600 may be a single layer of material, such as string or wire, or multiple layers of material. For example, the tethering snare 600 may be a braided or woven piece formed through multiple strings, wires, or the like.

Figure 7:
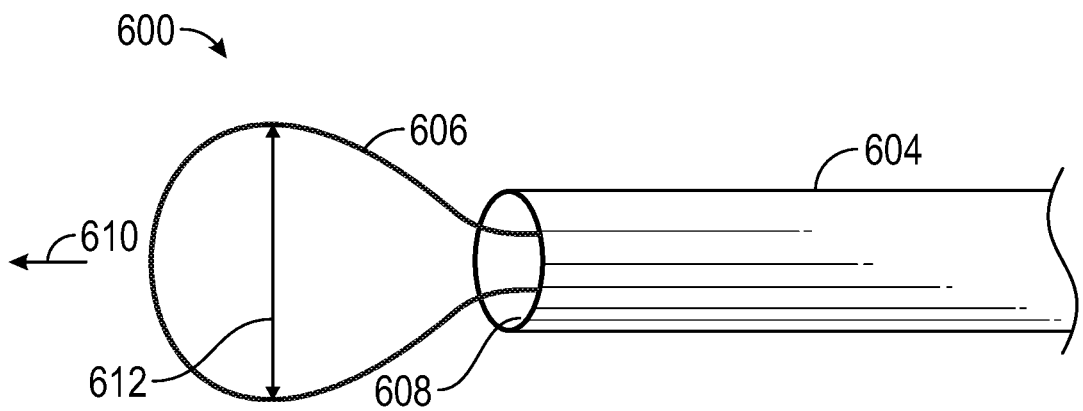
FIG. 7 illustrates a lateral view of a tethering snare extending from a distal end of a delivery catheter in an expanded state, according to an embodiment of the present disclosure.

FIG. 7 illustrates a lateral view of the tethering snare 600 extending from the distal end 602 of the delivery catheter 604 (which may be or include an IMD sheath) in an expanded state, according to an embodiment of the present disclosure. As shown in FIG. 7, the tethering snare 600 has been pushed, extended, or otherwise moved outwardly from the delivery catheter 604 in the direction of arrow 610. For example, the delivery catheter 604 (or an IMD sheath of the delivery catheter 604) may be pushed over the tethering snare 600 so that the tethering snare 600 retracts, contracts, recedes, retreats, or the like back into the delivery catheter 604. Conversely, the delivery catheter 604 may be retracted in relation to the tethering snare 600 so that the tethering snare 600 extends outwardly from the sheath. With increased urging of the tethering snare 600 in the direction of arrow 610, a diameter 612 of the loop 606 expands, enlarges, or otherwise increases.

Figure 8:
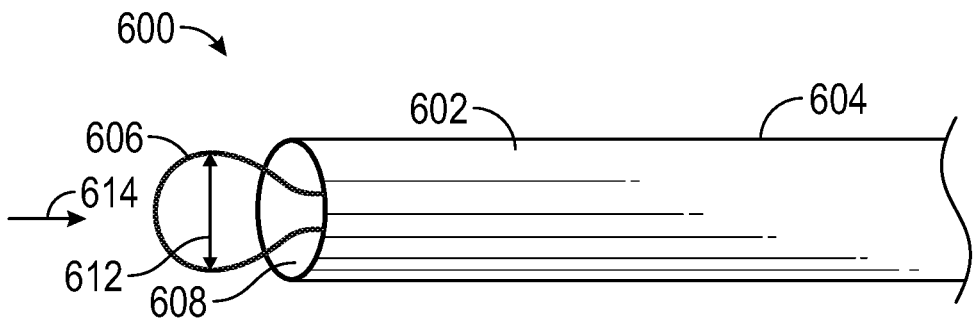
FIG. 8 illustrates a lateral view of a tethering snare extending from a distal end of a delivery catheter in a constricted state, according to an embodiment of the present disclosure.

FIG. 8 illustrates a lateral view of the tethering snare 600 extending from the distal end 602 of the delivery catheter 604 in a constricted state, according to an embodiment of the present disclosure. When the tethering snare 614 is drawn back into the internal passage 608 of the delivery catheter 604 in the direction of arrow 614, the diameter 612 of the loop decreases.

Figure 9:
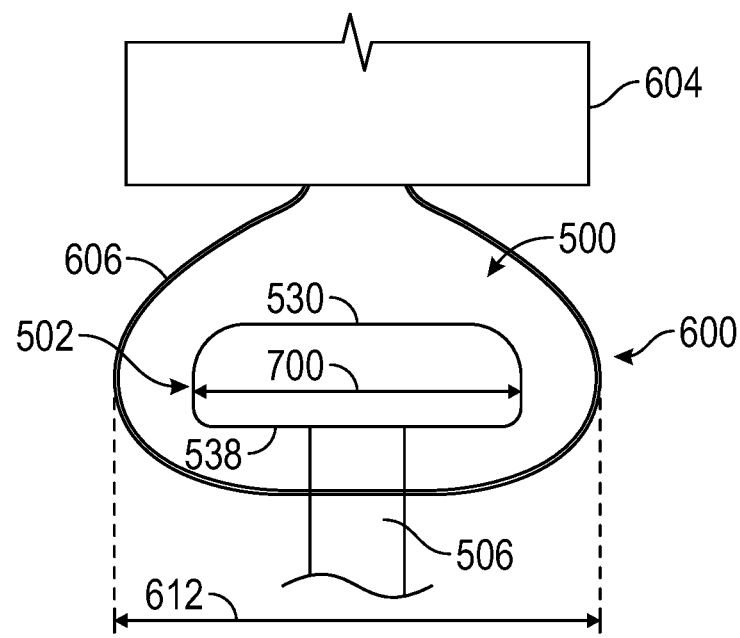
FIG. 9 illustrates a lateral view of a delivery catheter unsecured to an IMD, according to an embodiment of the present disclosure.

FIG. 9 illustrates a lateral view of the delivery catheter 604 unsecured to the IMD 500, according to an embodiment of the present disclosure. As shown in FIG. 9, the diameter 612 of the loop 606 of the tethering snare 600 is greater than the diameter 700 of the head 530 of the IMD 500. As such, the tethering snare 600 may pass over the head 530. In order to securely connect or tether the delivery catheter 604 to the IMD 500, a portion of the loop 606 may be positioned underneath the bottom surface 538 of the head 530. An operator may then draw the tethering snare 600 up into delivery catheter 604 (such as by pulling the tethering snare 600 into the delivery catheter 604, or sliding the delivery catheter 604 over the tethering snare 600) so that the diameter 612 is less than the diameter 700. In this manner, the tethering snare 600 is prevented from disconnecting from the attachment member 502. The loop 606 may then be further retracted so that it snugly wraps around the neck 506 of the attachment member 502 underneath the bottom surface 538 of the head 530.

Figure 10:
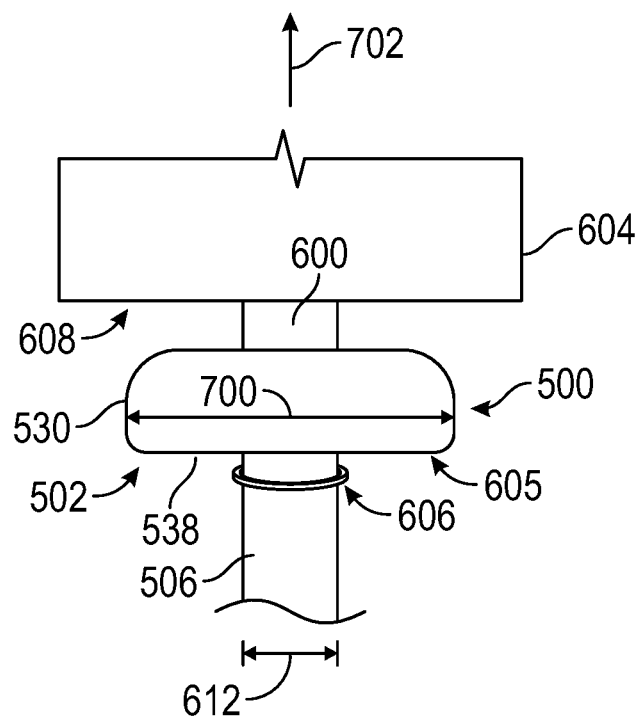
FIG. 10 illustrates a lateral view of a delivery catheter securely tethered to an IMD, according to embodiment of the present disclosure.

FIG. 10 illustrates a lateral view of the delivery catheter 604 securely tethered to the IMD 500, according to embodiment of the present disclosure. As shown, the tethering snare 600 is securely positioned at a connecting position 605, in which the retracted tethering snare 600 is wrapped around the neck 506 underneath the bottom surface 538 of the head 530. As such, the tethering snare 600 may constrict around the neck 506 at the connecting position 605. Because the diameter 612 of the loop 606 that extends outwardly from the delivery catheter 604 is less than the diameter 700 of the head 530, the tethering snare 600 remains secured to the IMD 500. As such, the IMD 500 is securely tethered to the delivery catheter 604.

In order to securely dock the IMD 500 to the delivery catheter 604, the tethered IMD 500 may be drawn up into the internal passage 608 of the delivery catheter 604 in the direction of arrow 610. Within the internal passage 608, the torque recesses 534 may mate with reciprocal torque keys within the delivery catheter 604.

In order to release the IMD 500 from the delivery catheter 604, the tethering snare 600 is pushed outwardly from the delivery catheter 604 so that the diameter 612 of the loop 606 exceeds the diameter 700 of the head 530, as shown in FIG. 9. As such, the loop 606 may pass over the head 530 in the direction of arrow 702 to disconnect the delivery catheter 604 from the IMD 500.

Figure 11:
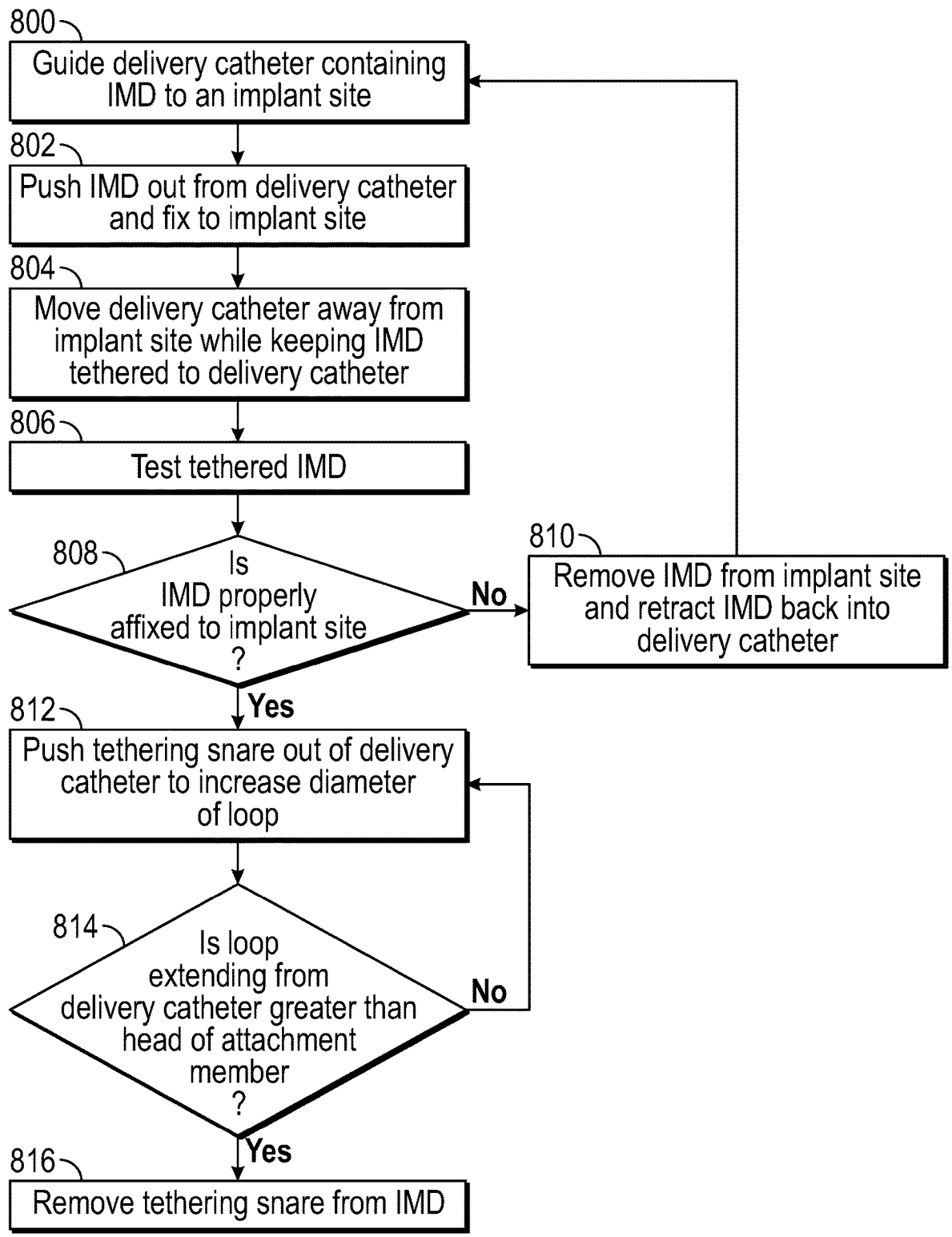
FIG. 11 illustrates a flow chart of a method of implanting an IMD at an implant site, according to an embodiment of the present disclosure.

FIG. 11 illustrates a flow chart of a method of implanting an IMD at an implant site, according to an embodiment of the present disclosure. The process begins at 800, in which a delivery catheter containing an IMD is guided to an implant site. Once at the implant site, the IMD is pushed out from the delivery catheter and fixed to the implant site at 802. Then, at 804, the delivery catheter is moved away from the implant site while remaining tethered to the IMD.

When the IMD is fixed to the implant site and tethered to the delivery catheter, the IMD is then tested at 806 to determine whether the IMD is properly physically and electrically connected to the implant site. At 808, it is determined whether the IMD is properly affixed to the implant site. If not, the method proceeds to 810, in which the IMD is removed from the implant site and retracted back into the delivery catheter and docked thereto. The process then returns to 800.

If, however, the IMD is properly affixed to the implant site, at 812, a tethering snare (which tethers the delivery catheter to the IMD) is pushed out of the delivery catheter to increase a diameter of a loop of the tethering snare. At 814, it is determined whether the loop extending from the delivery catheter is greater than a head of an attachment member of the IMD. If not, the process returns to 812. If, however, the loop extending from the delivery catheter is greater than the head of the attachment member, the tethering snare is removed from the IMD at 816, such as by slipping the loop over and off the attachment member, thereby releasing the IMD from the delivery catheter.

As described above, embodiments of the present disclosure provide a system and method for securing and releasing an IMD from a delivery catheter. The tethering snare may also be used to retrieve an IMD from an implanted position. The delivery catheter may include a tethering snare that may be extend out of, and retracted into, a locking sheath, for example, of the delivery catheter. The tethering snare is configured to expand to fit over the attachment member of the IMD, and then be constricted and tightened to securely tether to the attachment member.

It has been found that the embodiments described with respect to FIGS. 4-11 are less susceptible to changes in length (compared to known systems) that would otherwise occur due to changes in temperature, deflection, torsion, and the like. Additionally, the embodiments incorporate a delivery and retrieval system into a single system. For example, the tethering snare may be used to release the attachment member of the IMD, and securely re-connect the IMD to the delivery catheter. Further, the embodiments described with respect to FIGS. 4-11 are not susceptible to inadvertent, spontaneous release, for example.

Figure 12:
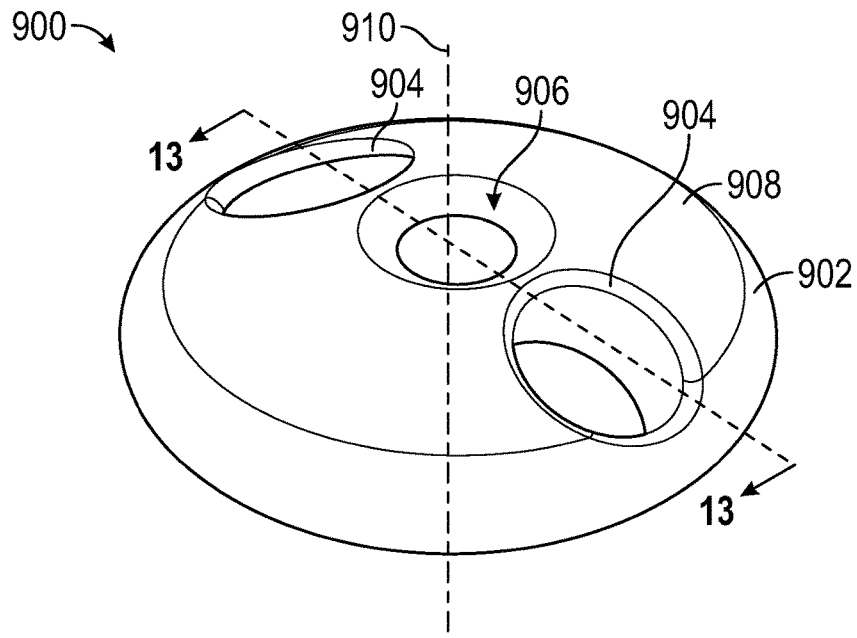
FIG. 12 illustrates a perspective top view of an attachment member of an IMD, according to an embodiment of the present disclosure.

FIG. 12 illustrates a perspective top view of an attachment member 900 of an IMD, according to an embodiment of the present disclosure. The attachment member 900 may be a part of the IMD. In at least one embodiment, the attachment member 900 may be a proximal end of a housing or can of the IMD. In at least one other embodiment, the attachment member 900 may fixedly or pivotally connect to the housing or can of the IMD through a neck, such as described above with respect to FIGS. 4 and 5.

The attachment member 900 may include a main body 902 having one or more torque recesses 904, as described above. A central passage 906 is formed through a top surface 908 of the main body 902. The central passage 906 may be aligned with and about a central axis 910 of the attachment member 900. The central passage 906 connects to an internal connection chamber formed within the main body 902.

Figure 13:
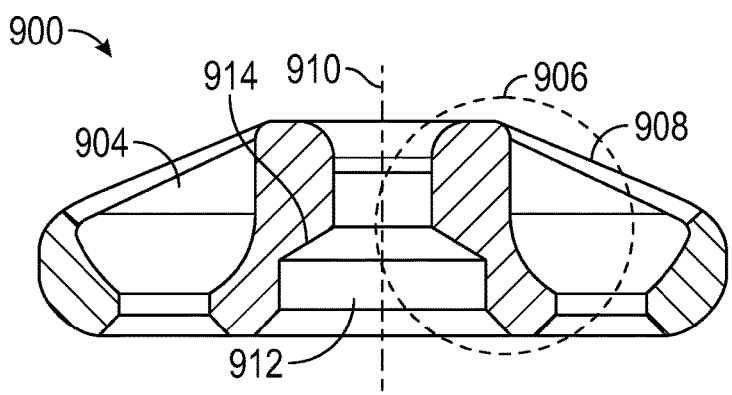
FIG. 13 illustrates a cross-sectional view of an attachment member of an IMD through line 13-13 of FIG. 12, according to an embodiment of the present disclosure.

FIG. 13 illustrates a cross-sectional view of the attachment member 900 of the IMD through line 13-13 of FIG. 12, according to an embodiment of the present disclosure. As shown, the central passage 906 connects to the internal connection chamber 912. The connection chamber 912 may be wider and larger than the central passage 906. For example, the connection chamber 912 may have a diameter that is twice that of the central passage 906. The central passage 906 may connect to the connection chamber 912 through outwardly flared walls 914. The flared walls 914 may angle outwardly and down from the central passage 906 to the connection chamber 912. Alternatively, the flared walls 914 may be flat walls that are perpendicular to the central axis 910.

As shown, an open channel may extend from the central passage 906 to the connection chamber 912. The open channel may be open-ended on both ends. Alternatively, the connection chamber 912 may be closed-ended.

As an example, the diameter of the central passage 906 may be 0.20". However, the diameter of the central passage 906 may be greater or less than 0.20".

Figure 14:
FIG. 14 illustrates a lateral view of a protuberance tether of a delivery catheter, according to an embodiment of the present disclosure.

FIG. 14 illustrates a lateral view of a protuberance tether 1000 of a delivery catheter, according to an embodiment of the present disclosure. The protuberance tether 1000 may include a flexible tether 1002 having a primary feature, expanded end, or protuberance 1004 at a distal end 1006. A proximal end 1007 of the tether 1002 may be operatively connected to a control device of an IMD delivery system, for example.

The protuberance 1004 may be a sphere, block, pyramid, or various other such protuberances that provides an interfering feature within a central passage of an attachment member. The protuberance 1004 has a diameter 1008 that is less than the diameter of the central passage 906 (shown in FIGS. 12 and 13). Accordingly, the protuberance 1004 may be sized and shaped to pass through the central passage 906.

As an example the diameter of the flexible tether 1002 may be 0.006", while the diameter of the protuberance may be 0.018". However, the diameter of the flexible tether 1002 may be greater or less than 0.006", while the diameter of the protuberance may be greater or less than 0.018".

Figure 15:
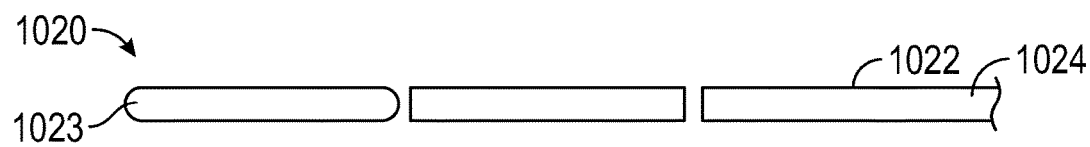
FIG. 15 illustrates a lateral view of a locking tether of a delivery catheter, according to an embodiment of the present disclosure.

FIG. 15 illustrates a lateral view of a locking tether 1020 of a delivery catheter, according to an embodiment of the present disclosure. The locking tether 1020 may include a flexible tether 1022 similar to the tether 1002. Notably, the locking tether 1020 does not include a protuberance at a distal end 1023. The locking tether 1020 may be featureless, and may be devoid of a protuberance. For example, the locking tether 1020 may be featureless in that it may merely be an elongated strand of material, such as string, wire, or the like, having a uniform diameter throughout or a different diameters at particular areas. The distal end 1023 may provide or otherwise be part of an elongated interfering segment that is configured to provide a blocking or interfering barrier within the central passage 906 of the attachment member 900. When disposed within the central passage 906, the elongated interfering segment prevents the protuberance 1004 from passing into the central passage 906. A proximal end 1024 of the tether 1022 may be operatively connected to a control device of an IMD delivery system, for example.

The elongated interfering segment may be the same diameter as the rest of the tether 1022, including the proximal end 1024. Optionally, the elongated interfering segment may be outwardly flared, or tapered in relation to the remainder of the tether 1022. Alternatively, a reduced-diameter extension may extend from a distal end of the elongated interfering segment. The reduced-diameter extension may have a diameter that is not great enough to block the protuberance 1008 from passing into and/or through the central passage 906.

As an example, the diameter of the flexible tether 1022 may be 0.006". However, the diameter of the flexible tether 1022 may be greater or less than 0.006".

Figure 16A:
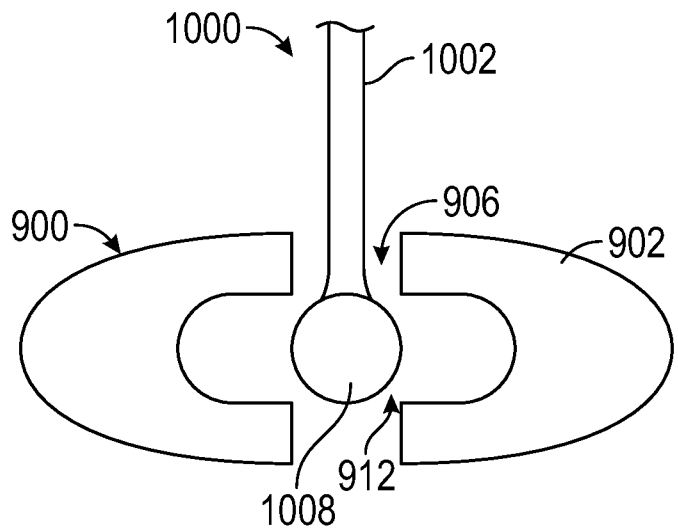
FIG. 16A illustrates a cross-sectional view of a protuberance tether passing into a connection chamber of an attachment member of an IMD, according to an embodiment of the present disclosure.

FIG. 16A illustrates a cross-sectional view of the protuberance tether 1000 passing into the connection chamber 912 of the attachment member 900 of the IMD, according to an embodiment of the present disclosure. As shown, the protuberance 1008 fits within the central passage 906 and is able to pass therethrough. In order to securely tether the delivery catheter to the IMD, the locking tether 1020 is passed into the central passage 906. The combined width of the locking tether 1020 and the protuberance 1008 within the central passage 906 and/or the connection chamber 912 is great enough to securely lodge the protuberance 1008 and the abutting portion of the locking tether 1020 within the central passage 906 and/or the connection chamber 912, thereby securely tethering the IMD to the delivery catheter.

Figure 16B:
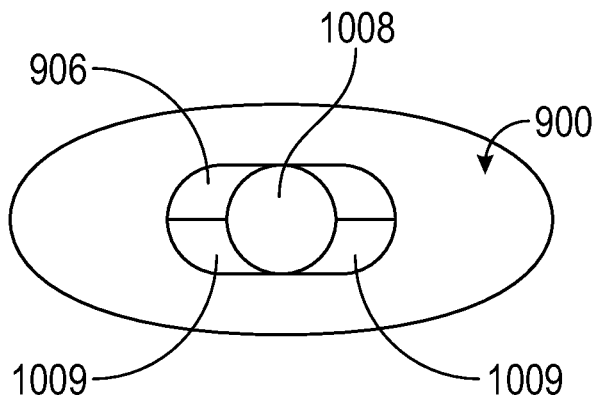
FIG. 16B illustrates an axial cross-sectional view of a protuberance within a central passage of an attachment member, according to an embodiment of the present disclosure.

FIG. 16B illustrates an axial cross-sectional view of the protuberance 1008 within the central passage 906 of the attachment member 900. It is to be understood that the view shown in FIG. 16B is simplified and is not necessarily drawn to scale. While in the central passage 906, a clearance area, gap, or the like 1009 is formed between an outer surface of the protuberance 1008 and an inner edge that defines the central passage 906. The clearance area 1009 provides a diametric clearance between the protuberance 1008 and the central passage 906 that allows the protuberance 1008 to pass therethrough. The clearance area 1009 is generally less than a diameter of the elongated interfering segment of the locking tether 1020. As such, when the elongated interfering segment of the locking tether 1020 is disposed within the central passage 906, the protuberance 1008 is blocked from passing therein.

Figure 16C:
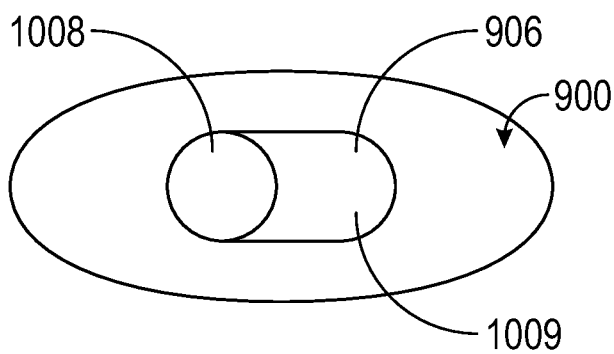
FIG. 16C illustrates an axial cross-sectional view of a protuberance within a central passage of an attachment member, according to an embodiment of the present disclosure.

FIG. 16C illustrates an axial cross-sectional view of the protuberance 1008 within the central passage 906 of the attachment member 900. It is to be understood that the view shown in FIG. 16c is simplified and is not necessarily drawn to scale. As shown, the protuberance 1008 may abut one side of a wall or edge portion that defines the central passage 906, but the total clearance area 1009 remains the same as shown in FIG. 16B.

Figure 17:
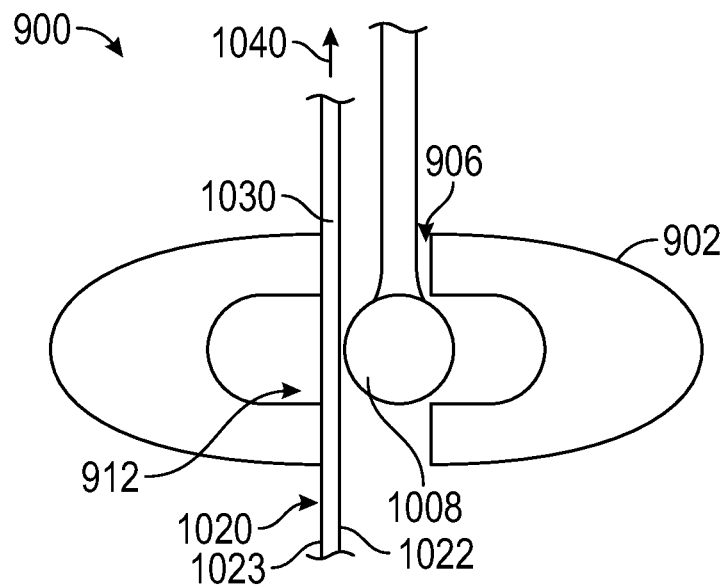
FIG. 17 illustrates a cross-sectional view of a protuberance tether and locking tether securely lodged within a connection chamber of an attachment member of an IMD, according to an embodiment of the present disclosure.

FIG. 17 illustrates a cross-sectional view of the protuberance tether 1002 and the locking tether 1020 securely lodged within the connection chamber 912 of the attachment member 900 of an IMD, according to an embodiment of the present disclosure. As shown, the combined width of the protuberance 1008 and the abutting portion 1030 of the locking tether 1020 lodges the protuberance 1008 within the connection chamber 912. As such, the tethers 1002 and 1020 are securely tethered to the attachment member 900. In this manner, the IMD is securely tethered to the delivery catheter.

As noted above, the locking tether 1020 may include a reduced-diameter extension, such as a string, that extends from a distal end of the elongated interfering segment 1023. The extension may be sized and shaped so that the protuberance 1008 may dislodge out of the attachment member 900 even when the extension is within the central passage 906.

Figure 18:
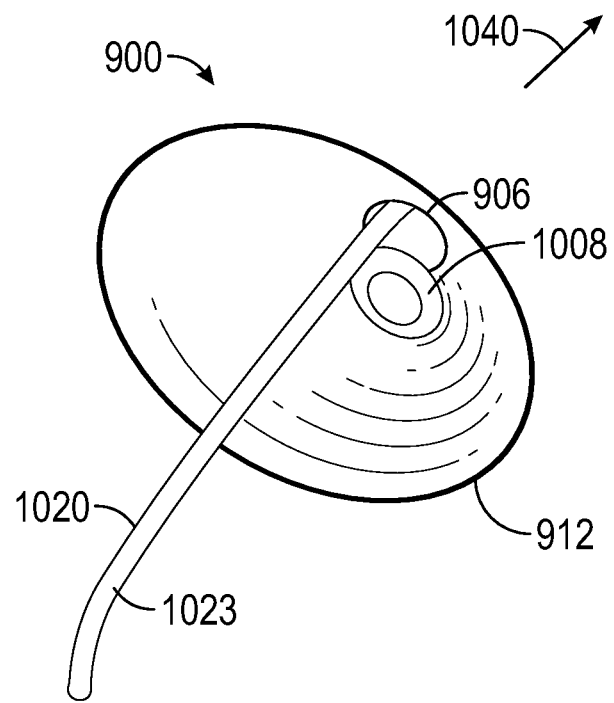
FIG. 18 illustrates a perspective bottom view of a protuberance of a protuberance tether and a locking tether securely lodged within a connection chamber of an attachment member of an IMD, according to an embodiment of the present disclosure.

FIG. 18 illustrates a perspective bottom view of a protuberance 1008 of a protuberance tether 1002 and a locking tether 1020 securely lodged within the connection chamber 912 of the attachment member 900 of an IMD, according to an embodiment of the present disclosure. Because the locking tether 1020 is positioned within the central passage 906, the protuberance 1008 is unable to pass through the central passage 906, and is instead lodged within the connection chamber 912. For example, because the combined diameter of the locking tether 1020 and the protuberance 1008 is greater than the diameter of the central passage 906, the protuberance 1008 is unable to pass into the central passage 906 when the locking tether 1020 is positioned therein.

Referring to FIGS. 17 and 18, in order to release the IMD from the delivery catheter, the elongated interfering segment 1023 of the locking tether 1020 is removed from the central passage 906 in the direction of arrow 1040. Once the locking tether 1020 is removed from the central passage 906, the protuberance 1008 may fit through the central passage 906. As such, the protuberance tether 1002 may also be removed from the central passage in the direction of arrow 1040, thereby releasing the IMD from the delivery catheter.

Continuing with the examples noted above, if the diameter of the central passage 906 is 0.020", and the diameter of the protuberance 1008 is 0.018", the protuberance 1008 is able to pass into the central passage 906. However, when the interfering segment 1023 of the locking tether 1020 is positioned within the central passage 906, the diameter of the interfering segment 1023 within the central passage 906 prevents the protuberance 1008 from passing into the central passage 906. For example, the combined diameter of the protuberance 1008 and the interfering segment 1023 is 0.024", which is greater than the 0.020" diameter of the central passage 906. Once the interfering segment 1023 is removed from the central passage 906, such as by being retracted into a delivery catheter, the protuberance 1008 may pop out of, or otherwise be removed from, the central passage 906. Note, however, that a reduced diameter portion extending from the interfering segment 1023 may still be in the central passage 906 when the protuberance 1008 is removed from the central passage 906. In this manner, the protuberance 1008 may be removed from the central passage 906 in response to the interfering segment 1023 of the locking tether 1020 being removed from the central passage 906.

Figure 19:
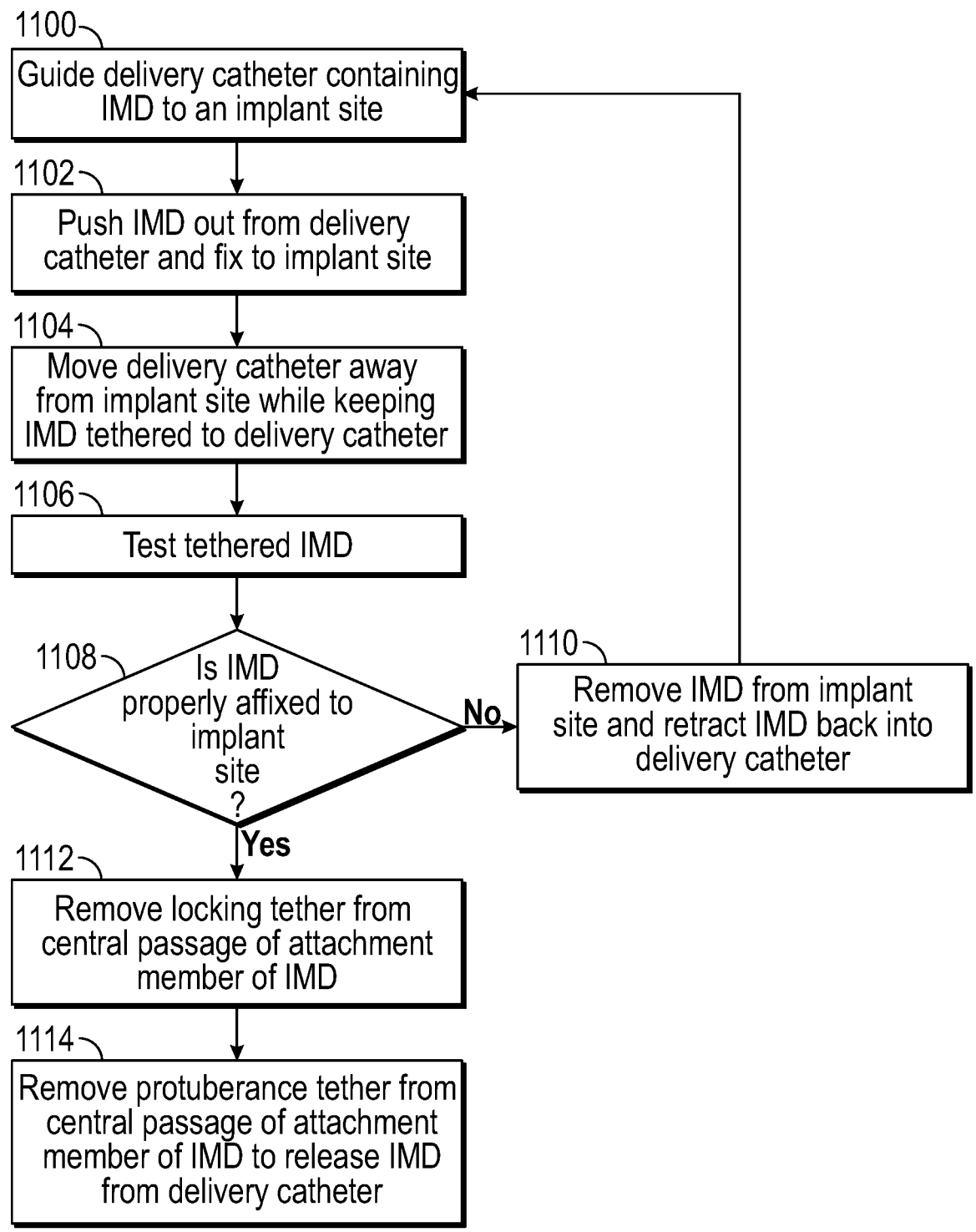
FIG. 19 illustrates a flow chart of a method of implanting an IMD at an implant site, according to an embodiment of the present disclosure.

FIG. 19 illustrates a flow chart of a method of implanting an IMD at an implant site, according to an embodiment of the present disclosure. The process begins at 1100, in which a delivery catheter containing an IMD is guided to an implant site. Once at the implant site, the IMD is pushed out from the delivery catheter and fixed to the implant site at 1102. Then, at 1104, the delivery catheter is moved away from the implant site while remaining tethered to the IMD.

When the IMD is fixed to the implant site and tethered to the delivery catheter, the IMD is then tested at 1106 to determine whether the IMD is properly physically and electrically connected to the implant site. At 1108, it is determined whether the IMD is properly affixed to the implant site. If not, the method proceeds to 1110, in which the IMD is removed from the implant site and retracted back into the delivery catheter and docked thereto. The process then returns to 1100.

If, however, the IMD is properly affixed to the implant site, the process continues to 1112, in which a locking tether of a delivery catheter is removed from a central passage of an attachment member of the IMD. Then, at 1114, a protuberance tether of the delivery catheter is removed from the central passage of the attachment member, thereby releasing the IMD from the delivery catheter.

It has been found that the embodiments described with respect to FIGS. 12-19 are less susceptible to changes in length (compared to known systems) that would otherwise occur due to changes in temperature, deflection, torsion, and the like. Further, the embodiments described with respect to FIGS. 12-19 are not susceptible to inadvertent, spontaneous release, for example.

Figure 20:
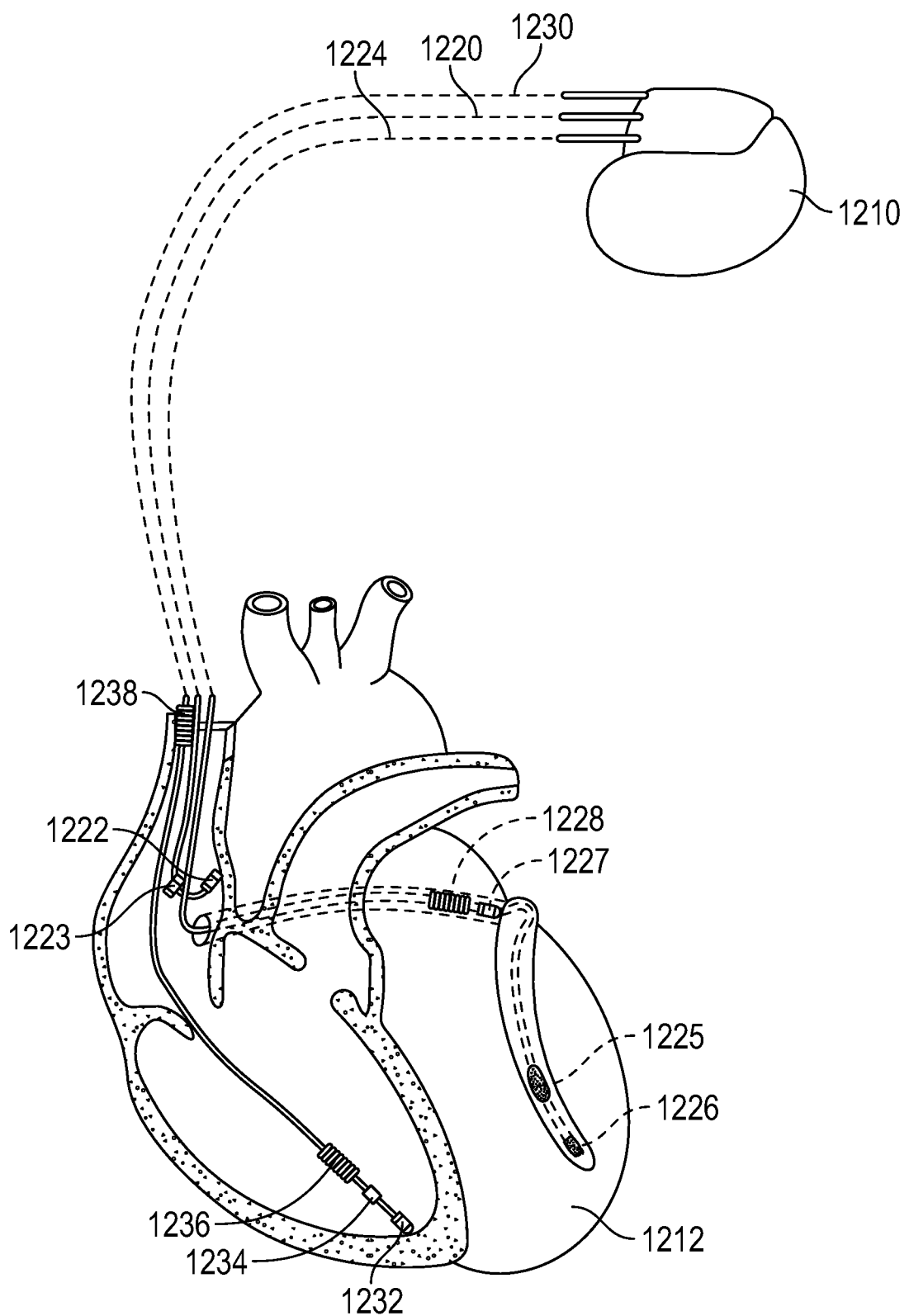
FIG. 20 illustrates a simplified view of an IMD in electrical communication with at least three leads implanted into a patient's heart, according to an embodiment.

FIG. 20 illustrates a simplified view of an IMD 1210 in electrical communication with at least three leads 1220, 1224, and 1230 implanted into a patient's heart 1212, according to an embodiment. The IMD 1210 may be implanted into the heart 1212 and released from a delivery catheter, such as described above with respect FIGS. 1-19.

To sense atrial cardiac signals and to provide right atrial chamber stimulation therapy, the IMD 1210 may be coupled to an implantable right atrial lead 1220 including at least one atrial tip electrode 1222 that typically is implanted in the patient's right atrial appendage. The right atrial lead 1220 may also include an atrial ring electrode 1223 to allow bipolar stimulation or sensing in combination with the atrial tip electrode 1222.

To sense the left atrial and left ventricular cardiac signals and to provide left-chamber stimulation therapy, the IMD 1210 may be coupled to a lead 1224 designed for placement in the "coronary sinus region" via the coronary sinus ostium in order to place a distal electrode adjacent to the left ventricle and additional electrode(s) adjacent to the left atrium. As used herein, the phrase "coronary sinus region" refers to the venous vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, the lead 1224 is designed to: receive atrial and/or ventricular cardiac signals; deliver left ventricular pacing therapy using at least one left ventricular tip electrode 1226 for unipolar configurations or in combination with left ventricular ring electrode 1225 for bipolar configurations; deliver left atrial pacing therapy using at least one left atrial ring electrode 1227 as well as shocking therapy using at least one left atrial coil electrode 1228.

The IMD 1210 is also shown in electrical communication with the patient's heart 1212 by way of an implantable right ventricular lead 1230 including, in the embodiment, a right ventricular (RV) tip electrode 1232, a right ventricular ring electrode 1234, a right ventricular coil electrode 1236, a superior vena cava (SVC) coil electrode 1238, and so on. Typically, the right ventricular lead 1230 is inserted transvenously into the heart 1212 so as to place the right ventricular tip electrode 1232 in the right ventricular apex such that the RV coil electrode 1236 is positioned in the right ventricle and the SVC coil electrode 1238 will be positioned in the right atrium and/or superior vena cava. Accordingly, the right ventricular lead 1230 is capable of receiving cardiac signals, and delivering stimulation in the form of pacing and shock therapy to the right ventricle.

The IMD 1210 may be one of various types of implantable devices, such as, for example, an implantable pacemaker, implantable cardioverter-defibrillator ("ICD"), defibrillator, cardiac rhythm management ("CRM") device, neurostimulator, electrophysiology ("EP") mapping and radio frequency ("RF") ablation system, or the like.

While various spatial and directional terms, such as top, bottom, lower, mid, lateral, horizontal, vertical, front and the like may be used to describe embodiments of the present disclosure, it is understood that such terms are merely used with respect to the orientations shown in the drawings. The orientations may be inverted, rotated, or otherwise changed, such that an upper portion is a lower portion, and vice versa, horizontal becomes vertical, and the like.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the disclosure without departing from its scope. While the dimensions, types of materials and coatings described herein are intended to define the parameters of the disclosure, they are by no means limiting and are exemplary embodiments. Many other embodiments will be apparent to those of skill in the art upon reviewing the above description. The scope of the disclosure should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means—plus-function format and are not intended to be interpreted based on 35 U.S.C. § 112(f), unless and until such claim limitations expressly use the phrase "means for" followed by a statement of function void of further structure.

The invention claimed is:

1. A system for implanting an implantable medical device (IMD) within a patient, the system comprising:
   a delivery catheter including first and second tethers that may be moved outwardly from and retracted into the delivery catheter, wherein the first tether includes a protuberance at a first distal end, and wherein the second tether includes an elongated interfering segment at a second distal end; and
   an IMD including a housing and an attachment member, wherein the attachment member includes a neck extending from the housing, and an expanded head connected to the neck and having a central passage connected to a connection chamber within the expanded head, wherein the connection chamber is wider than the central passage and longer than the protuberance such that the protuberance is lodged within the connection chamber to securely tether the IMD to the delivery catheter when the elongated interfering segment is moved outwardly from the delivery catheter and positioned in the central passage, and wherein the protuberance is configured to dislodge from the connection chamber when the elongated interfering segment is retracted into the delivery catheter and removed from the central passage.

2. The system of claim 1, wherein the elongated interfering segment is devoid of any protuberance, and wherein a combined diameter of the protuberance and the elongated interfering segment is greater than a passage diameter of the central passage.

3. The system of claim 1, wherein a protuberance diameter of the protuberance is less than a passage diameter of the central passage.

4. The system of claim 3, wherein a tether diameter of the elongated interfering segment of the second tether is less than either of the passage diameter and the protuberance diameter.

5. The system of claim 4, wherein a combined diameter of the tether diameter and the protuberance diameter is greater than the passage diameter.

6. A method for implanting an implantable medical device (IMD) within a patient, the method comprising:
   securing the IMD to a delivery catheter by positioning a first tether of the delivery catheter within a central passage of an attachment member of the IMD, wherein the attachment member includes a neck extending from a housing of the IMD, an expanded head connected to the neck, and a central passage connected to a connection chamber within the expanded head, and wherein the connection chamber is wider than the central passage and longer than a protuberance such that positioning the first tether within the central passage lodges the protuberance within the connection chamber; and
   releasing the IMD from the delivery catheter by removing the first tether from the central passage, wherein removing the first tether from the central passage allows the protuberance to dislodge from the connection chamber and to be removed from the central passage.

7. The method of claim 6, wherein a protuberance diameter of the protuberance is less than a passage diameter of the central passage.

8. The method of claim 7, wherein a tether diameter of the first tether is less than either of the passage diameter and the protuberance diameter, and wherein a combined diameter of the tether diameter and the protuberance diameter is greater than the passage diameter.

9. The system of claim 1, wherein the neck is pivotally secured to the housing.

10. The system of claim 1, wherein the attachment member includes at least one torque recess.

11. The system of claim 6, wherein the neck is pivotally secured to the housing.

12. The system of claim 6, wherein the attachment member includes at least one torque recess.

13. The system of claim 6, wherein the first tether is devoid of any protuberance, and wherein a combined diameter of the protuberance and the first tether is greater than a passage diameter of the central passage.

* * * * *